United States Patent [19]

Komiya

[11] 4,011,872
[45] Mar. 15, 1977

[54] ELECTRICAL APPARATUS FOR TREATING AFFECTED PART IN A COELOMA

[75] Inventor: Osamu Komiya, Hachioji, Japan

[73] Assignee: Olympus Optical Co., Ltd., Tokyo, Japan

[22] Filed: Mar. 28, 1975

[21] Appl. No.: 563,071

[30] Foreign Application Priority Data

Apr. 1, 1974 Japan .............................. 49-37269
Apr. 1, 1974 Japan .............................. 49-37270

[52] U.S. Cl. .......................... 128/303.14; 128/321
[51] Int. Cl.² ....................................... A61B 17/36
[58] Field of Search ................. 128/303.14, 303.13, 128/303.15–303.18, 407–409, 321

[56] References Cited

UNITED STATES PATENTS

| 1,731,069 | 10/1929 | Herman | 128/303.16 |
| 2,102,270 | 12/1937 | Hyams | 128/303.17 |
| 3,100,489 | 8/1963 | Bagley | 128/303.17 |
| 3,805,791 | 4/1974 | Sueberth et al. | 128/303.14 |
| 3,831,607 | 8/1974 | Lindemann | 128/303.17 |
| 3,858,586 | 1/1975 | Lessen | 128/303.17 |

FOREIGN PATENTS OR APPLICATIONS 664,359   3/1928   France .............................. 128/407

*Primary Examiner*—Robert W. Michell
*Assistant Examiner*—Lee S. Cohen
*Attorney, Agent, or Firm*—Ostrolenk, Faber, Gerb & Soffen

[57] ABSTRACT

An apparatus comprises an electrode operating member which is disposed within the distal end portion of an electrically insulating flexible tube which is adapted to be inserted into a coeloma. A plurality of electrodes for treating an affected part are attached to the electrode operating member, which is in turn moved by an operating wire passing through the tube, thereby enabling a movement of the electrodes out of or back into an opening formed in the end of the flexible tube. A high frequency current is supplied to the electrodes through the operating wire or a separate power cable.

10 Claims, 17 Drawing Figures

ELECTRICAL APPARATUS FOR TREATING AFFECTED PART IN A COELOMA

BACKGROUND OF THE INVENTION

The invention relates to an electrical apparatus for treating an affected part in a coeloma, and more particularly to an electrical apparatus for surgically treating an affected part in a coeloma of a human body with a high frequency current.

An electrical apparatus for surgically treating diseased tissue by the use of a high frequency current is commonly known as a radio knife, and has been used only for the treatment of the exposed affected part of a physical body. However, with the recent development of endoscopes for examining the interior of a coeloma, a high frequency treatment of an affected part within a coeloma is contemplated. A radio knife which is designed to this end comprises a single treating electrode which is introduced into the coeloma, while the other electrode is brought in contact with the skin of a patient over an extensive area, thereby concentrating the electric current in the region of contact of the treating electrode for the purpose of excision, erasion or coagulation of the tissue in such region. However, such apparatus has an unsatisfactory efficiency and treating capability, and is also limited in the shape and number of treating electrodes, whereby inconveniences are experienced in providing a desired treatment effectively. Specifically, a large spacing between the electrodes may cause a cautery of tissues other than the affected one which need not be cauterized. Thus, the apparatus suffers from the inability of providing a localized treatment.

SUMMARY OF THE INVENTION

It is an object of the invention to provide an electrical apparatus for treating an affected part in a coeloma including a plurality of electrodes for treating affected part, which electrodes are all introduced into a coeloma by passing them through an electrically insulating flexible tube and which are supplied with a high frequency current through a power cable that is also passed through the flexible tube, the maneuvering of the treating electrodes being improved through the use of an operating wire to thereby produce an effective high frequency treatment of the affected part in a coeloma.

In accordance with the invention, an electrode operating member provided with a plurality of treating electrodes is mounted in the distal end portion of an electrically insulating flexible tube which is introduced into a coeloma, and the electrodes are supplied with a high frequency current from a high frequency source through a power cable which is also passed through the flexible tube. In accordance with the invention, a maneuvering of the treating electrodes within the coeloma is achieved in a facilitated manner, and the localized treating capability is increased, eliminating the disadvantage of cauterizing deep tissues which do not require cautery. At least one of the treating electrodes which is connected with one terminal of the high frequency source is coated with an electrically insulating material except for its end portion which remains exposed for contact with the tissue in the coeloma, thus preventing a direct contact between the treating electrodes and assuring an effective localized treatment of only an intended part. It is found that the treated tissue recovers rapidly.

DETAILED DESCRIPTION OF THE PREFERRED EMBODIMENT OF THE INVENTION

Figure 1:
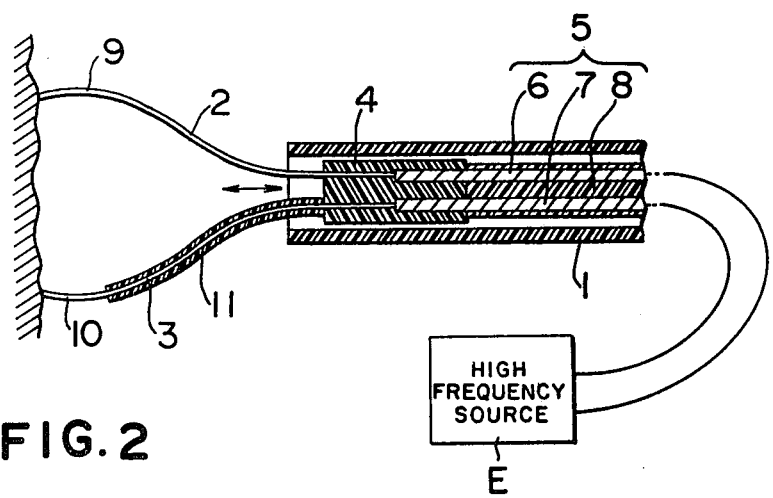
FIG. 1 is a cross section of the electrical apparatus for treating affected part in a coeloma which is constructed in accordance with a first embodiment of the invention.

FIG. 1 is a cross section of the electrical apparatus for treating an affected part in a coeloma which is constructed in accordance with a first embodiment of the invention. The apparatus includes an electrically insulating flexible tube 1 which is shaped so that it can be introduced into a coeloma by passing it through a forceps channel of an endoscope. A plurality of electrodes 2, 3 for treating an affected part is attached to an electrode operating member 4, which electrodes 2, 3 are mounted in the forward end of the flexible tube 1. The electrode operating member 4 comprises an electrically insulating material and is mechanically connected with a power cable 5 which passes through the flexible tube 1. At its other end, the power cable 5 extends out of the flexible tube 1, and can be operated to advance or retract the electrode operating member 4 within the flexible tube 1. Thus, the power cable 5 functions as an operating wire. The cable 5 comprises a pair of electrically conductive wires 6, 7 which are connected with the terminals of a high frequency source E and which are covered with and integrally molded with an electrically insulating resin 8 which both separates and surrounds wires 6 and 7.

Figure 4:
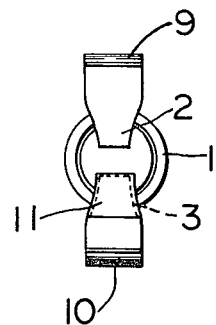
FIG. 4 is a front view of the forward portion of the apparatus shown in FIG. 1.
Figure 5:
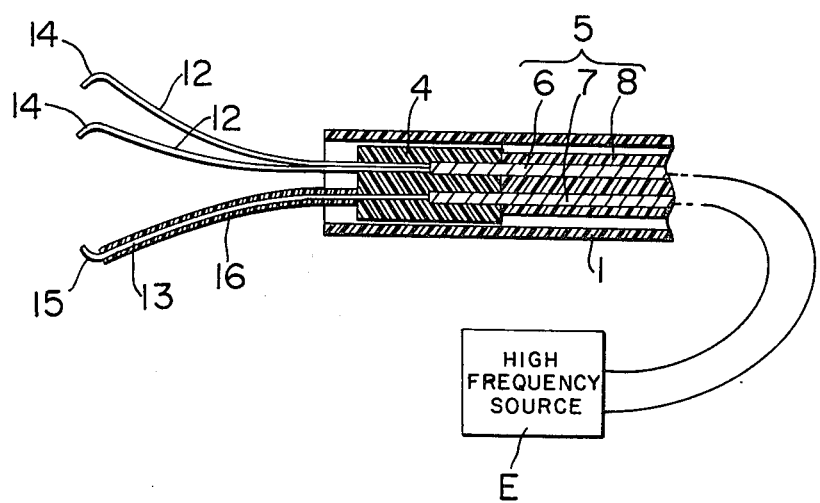
FIG. 5 is a cross section of the electrical apparatus for treating affected part in a coeloma which is constructed in accordance with a second embodiment of the invention.
Figure 6:
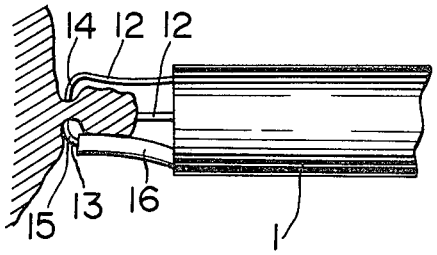
FIG. 6 is a similar view to FIGS. 2 and 3, but illustrating the operation of the apparatus shown in FIG. 5.

The treating electrodes 2, 3 are formed of strips of electrically conductive material and attached to the electrode operating member 4 in opposing relationship with each other, with their forward free ends 9, 10 normally resiliently urged away from each other. As shown in FIG. 4, the portions of the electrodes 2, 3 inward from the forward free ends 9, 10 are more closely spaced than the forward free ends 9, 10. The forward free ends 9, 10 have a width which is slightly less than the internal diameter of the flexible tube 1 so that by pulling the power cable 5, the treating electrodes 2, 3 can be retracted into the flexible tube 1 together with the electrode operating member 4, the electrodes 2, 3 being then constrained by the edge of the opening of the tube 1 to be positioned closer to each other when the member 4 is drawn into tube 1. When the electrodes 2, 3 are pushed forward, they assume an open position shown in FIG. 1, by virtue of their inherent resilience. In order to increase the retention of tissue between the electrodes 2, 3, their forward ends 9, 10 are gently curved toward each other at their tips. The electrodes 2, 3 are electrically connected with the conductive wires 6, 7 of the power cable 5 within the electrode operating member 4. One of the treating electrodes, 3, is coated with an electrically insulating material 11 except for the forward end 10 which remains exposed. Thus, no direct contact occurs between the electrodes 2, 3 except for the forward ends 9, 10 which bear against the opposite sides of the tissue of an affected part.

Figure 2:
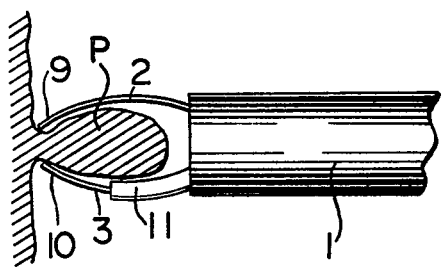
FIGS. 2 and 3 are similar views to FIG. 1, illustrating the operation of the apparatus shown in FIG. 1.
Figure 3:
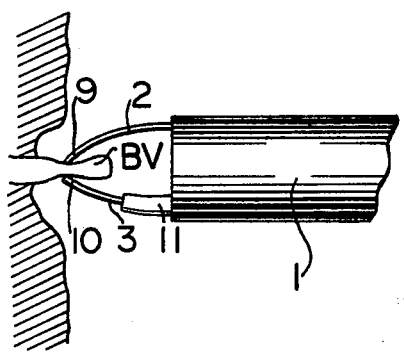

In use, the operating wire or the power cable 5 is pulled to retract the electrode operating member 4 together with the treating electrodes 2, 3 into the flexible tube 1, and the flexible tube 1 is passed through the forceps channel of an endoscope, for example, to move it to an intended region within a coeloma. Then the power cable 5 is externally operated to push forward the electrode operating member 4 as shown in FIG. 1, causing the treating electrodes 2, 3 to move out of the opening in the inner end of the flexible tube 1. The degree of opening of the treating electrodes 2, 3 depends on the amount of such movement. FIG. 1 illustrates the maximum opening, and at this time the electrodes 2, 3 are removed from contact with the edge of the opening in the flexible tube 1. Where a cautery and coagulation of the tissue in the coeloma is desired over a broad area, the electrodes 2, 3 are opened as shown in FIG. 1, and their forward free ends 9, 10 are brought into contact with the surface of the tissue, followed by energization thereof through the power cable 5 by operating the high frequency source E. Thereupon a high frequency current flows through the tissue portion lying between the forward ends 9, 10 of the electrodes 2, 3, producing a Joule's heat therein by virtue of the electrical resistance presented by the tissue portion, thereby accomplishing the cautery and coagulation of the tissue portion between the forward ends 9, 10. The spacing between the forward ends 9, 10 of the electrodes 2, 3 can be adjusted to any desired opening by pulling the cable 5 to cause the electrodes 2, 3 to bear against the edge of the opening in the flexible tube 1. In this manner, the area over which the cautery or coagulation is performed can be determined as desired. A cautery or coagulation of part of the tissue in the coeloma, such as polyp or blood vessel, can be achieved by holding the polyp P (FIG. 2) or blood vessel BV (FIG. 3) between the end portions 9, 10 and producing a current flow therebetween.

Figure 7:
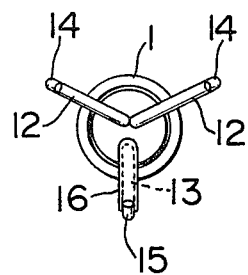
FIGS. 7 and 8 are front views, illustrating two arrangements of the apparatus shown in FIG. 5 and having different numbers of the treating electrodes.
Figure 8:
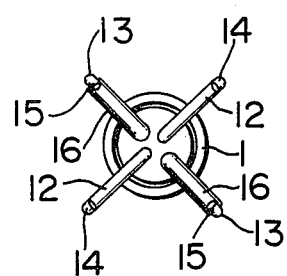

FIGS. 5 to 8 show a second embodiment of the invention in which a plurality of treating electrodes are all formed of rod-shaped resilient conductive material. FIG. 7 shows the use of three treating electrodes 12, 12, 13 while FIG. 8 shows the use of four electrodes 12, 12, 13, 13. As in the first embodiment, the electrodes 12, 13 are resiliently urged to assume an open position so as to be spaced apart from each other, and their forward ends 14, 15 are folded back toward each other. The electrode 13 or electrodes 13, 13 which are connected with one terminal of the high frequency source E are coated with an electrically insulating material 16 except for their forward ends 15 which remain exposed, thus minimizing the possibility of electrical contact with the other electrodes 12. In other respects, the arrangement and function are generally similar to those described in connection with the first embodiment.

Figure 9:
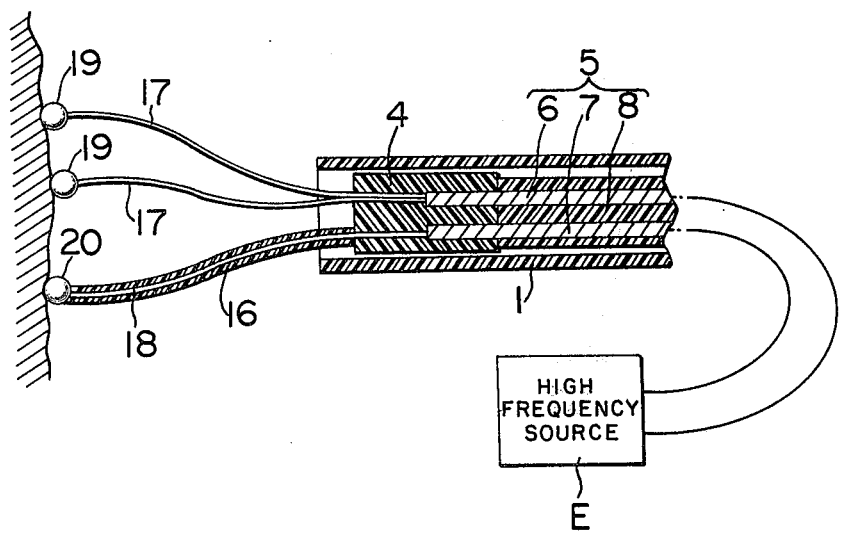
FIG. 9 is a cross section of the electrical apparatus for treating affected part in a coeloma which is constructed in accordance with a third embodiment of the invention.
Figure 10:
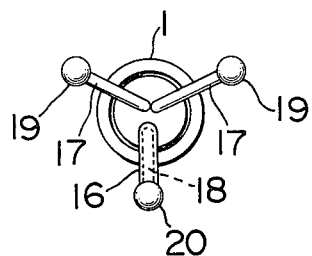
FIG. 10 is a front view of the forward portion of the apparatus shown in FIG. 9.
Figure 11:
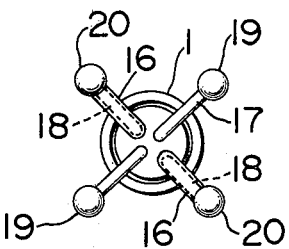
FIG. 11 is a front view of an apparatus similar to that shown in FIG. 9, but having a different number of electrodes.

FIGS. 9 to 11 show a third embodiment of the invention in which treating electrodes 17, 18 have their forward tips 19, 20 formed as spheres for increasing the area of contact with the tissue within the coeloma. Other features are similar to those described previously.

Figure 12:
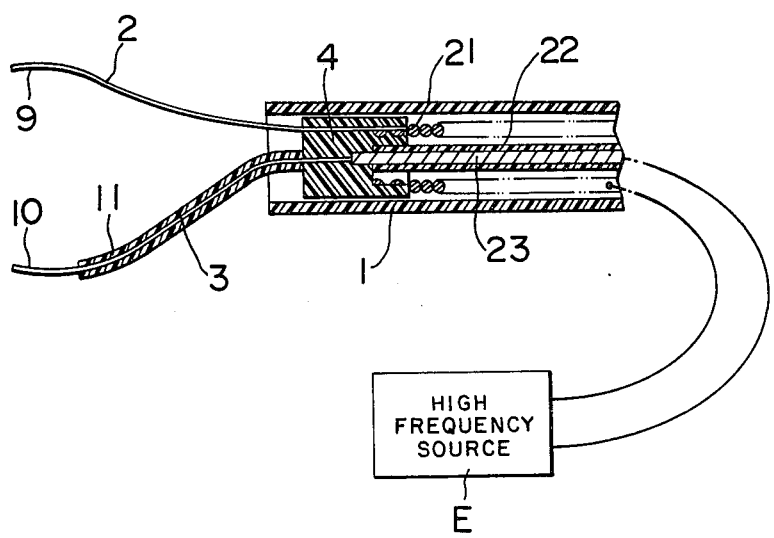
FIG. 12 is a cross section of the electrical apparatus for treating affected part in a coeloma which is constructed in accordance with a fourth embodiment of the invention.

FIG. 12 shows a fourth embodiment of the invention, illustrating a modification of the power cable or operating wire which operates on the electrode operating member 4. Specifically, the cable comprises an electrically conductive coil 21 which is inserted into the flexible tube 1, and an electrically conductive wire 23 covered with an electrically insulating material 22 and passing inside the coil 21. The coil 21 and the wire 23 are secured to the electrode operating member 4 and are electrically connected with the electrodes 2, 3, respectively. In this manner, the overall flexibility of the device is increased, improving the maneuverability. In other respects, the arrangement and function are similar to those described previously in connection with the first and second embodiments.

Figure 13:
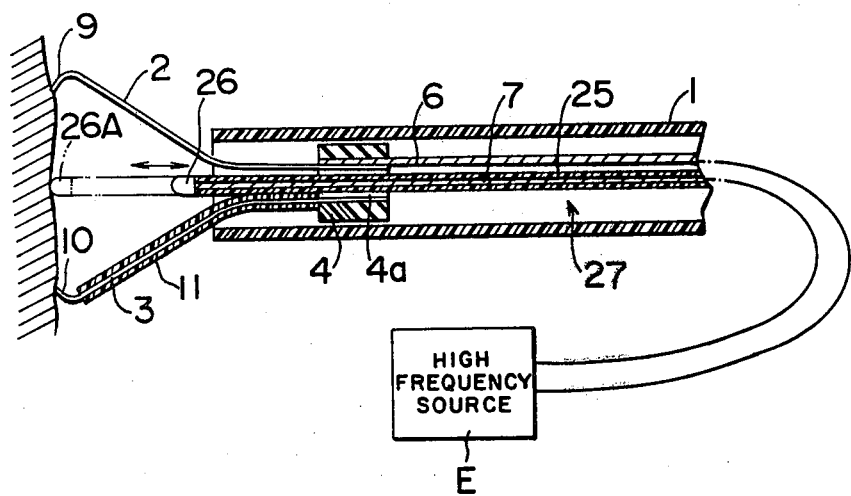
FIG. 13 is a cross section of the electrical apparatus for treating affected part in a coeloma which is constructed in accordance with a fifth embodiment of the invention.
Figure 14:
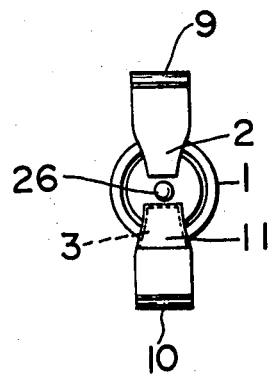
FIG. 14 is a front view of the forward portion of FIG. 13.

FIGS. 13 and 14 show a fifth embodiment of the invention in which the electrode operating member 4 is mechanically connected with a conductive operating wire 6 which passes through the flexible tube 1. The wire 6 projects out of the other or opposite end of the flexible tube 1, and can be operated to cause a displacement of the electrode operating member 4. In addition, the wire 6 is electrically connected with both treating electrodes 2, 3. Thus the operating wire 6 constitutes one of the supply wires within the power cable. Another conductive operating wire 7 covered with an insulating material 25 passes through the center of the flexible tube 1, and extends through an opening 4a formed centrally in the electrode operating member 4 so that its forward end extends into the opening of the flexible tube 1. A treating electrode 26 formed of a conductive material and having a spherical configuration is attached to the extremity of the conductive operating wire 7. At its other end, the operating wire 7 also extends out of the other end of the flexible tube 1 to permit an advancing or retracting operation of the treating electrode 26. When the operating wire 7 is forced into the flexible tube 1, the treating electrode 26 can be projected into the space between the other treating electrodes 2, 3. The operating wire 7 constitutes the other supply wire of the power cable, and is electrically connected with the other terminal of the source E for energizing the electrode 26. In the arrangement described, the wires 6, 7 serve as the supply wires of the power cable 27 while simultaneously functioning as the operating wires. Alternatively, the operating wires 6, 7 may be separate from the power cable 27 so as to serve only the electrode operating function.

In use, the respective treating electrodes 2, 3, 26 are initially retracted within the flexible tube 1, which is then inserted into the forceps channel of an endoscope, for example, for introducing it to an intended region within a coeloma. Subsequently, the operating wire 6 is externally operated to advance the electrode operating member 4 forward, thereby projecting the treating electrodes 2, 3 of one polarity out of the opening of the flexible tube 1. At this time, since the electrodes 2, 3 bear against the edge of the opening in the flexible tube 1, the degree of opening of the electrodes 2, 3 depends on the extent to which the electrodes 2, 3 are projected. In FIG. 13, the maximum separation distance between electrodes 2, 3 is shown, and under this condition, displaced from the left-hand edge of the opening in of the flexible tube 1. The degree of separation of these electrodes are adjusted according to the size of an area for which a cautery or coagulation treatment is desired. After such adjustment, the forward ends 9, 10 of the treating electrodes 2, 3 are brought into contact with the surface of the tissue in the coeloma. Subsequently, the operating wire 17 is externally operated to cause the treating electrode 26 of the opposite polarity to project through the opening in the flexible tube 1 so as to contact the surface of the tissue at a position intermediate the remaining electrodes 2, 3, as indicated in phantom lines 26A in FIG. 13. Then the source E is turned on to supply a high frequency current to the respective electrodes 2, 3, 26, whereupon the tissue portion lying between the electrodes 2, 3 and the electrode 26 are cauterized or coagulated by the Joule's heat produced.

Figure 15:
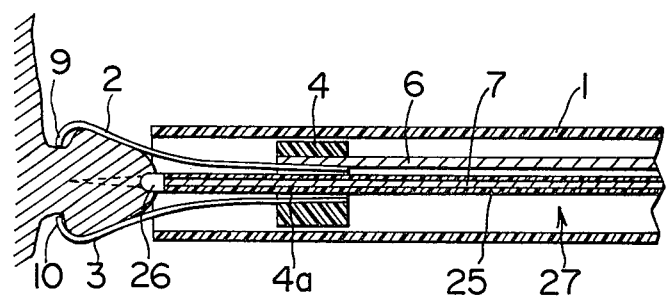
FIG. 15 is a cross section of the apparatus shown in FIG. 13, illustrating the operation thereof.

FIG. 15 shows a modification in which part of the tissue in a coeloma is held between the forward ends 9, 10 of the treating electrodes 2, 3 of one polarity while the treating electrode 26 of the other polarity is applied against the top of the tissue for cautery and coagulation. In this manner, it is possible to produce a cautery and coagulation of the entire tissue portion which is held between the electrodes 2, 3. Such an arrangement is useful for the cautery and coagulation of an affected part, such as a polyp. The cauterized and coagulated tissue portion will be destroyed and the removed dead tissue falls down. An even more complete cautery of the tissue portion held between the electrodes 2, 3 can be achieved by providing the electrode 26 in the form of a needle, as indicated in broken lines in FIG. 15.

Figure 16:
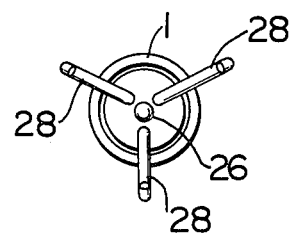
FIGS. 16 and 17 are front views of modifications of the embodiments of FIG. 15.
Figure 17:
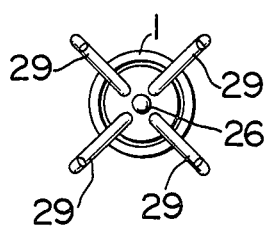

FIGS. 16 and 17 illustrate an arrangement in which a plurality of electrodes 28, 29 of one polarity are in the form of resilient conductive rods and cooperate with the centrally located electrode 26. It will be understood that these electrodes 28, 29 open to a degree dependent on the extent by which they project from the forward end of the flexible tube 1.

What is claimed is:

1. An electrical apparatus for treating an affected part in a coeloma comprising:
    an electrically insulating, hollow, flexible tube having a distal end and a proximal end and adapted to be inserted into a coeloma and having an opening in its distal end;
    an electrode operating member formed of an insulating material and having a first end facing said distal end of said flexible tube and a second end facing said proximal end of said flexible tube, said electrode operating member being slidably disposed within said flexible tube such that said electrode operating member can slide towards and away from said distal end of said flexible tube;
    a plurality of treating electrodes each being formed of a resilient, conductive material, each of said treating electrodes having a free end and a base end, said base ends of said treating electrodes being attached to said first end of said electrode operating member, said free ends of said treating electrodes extending towards said opening in said flexible tube for movement out of and into said opening in said flexible tube in response to movement of said electrode operating member;
    an operating wire extending from said proximal end of said flexible tube into said flexible tube and secured to said second end of said electrode operating member for causing displacement of said electrode operating member in response to displacement of said operating wire into and out of said flexible tube, said operating wire including power cable means for supplying a high frequency current to the treating electrodes.

2. An electrical apparatus according to claim 1 in which at least one of the treating electrodes is covered with an electrically insulating material over the length of said one electrode which is located externally of the electrode operating member except for the extreme end portion of the free end which remains exposed for cooperation with another one of the electrodes to hold a portion of a tissue in a coeloma therebetween, thus preventing direct contact between the cooperating electrodes.

3. An electrical apparatus according to claim 1 in which the tip of the free ends of each treating electrode is made spherical to increase the area of contact with a tissue in the coeloma.

4. An electrical apparatus according to claim 1 in which a pair of said treating electrodes are formed of conductive blades each including a free end of a width slightly less than the internal diameter of the flexible tube and a base end at which it is attached to the electrode operating member, the width of the base end being reduced as compared with the width of the free end, said electrodes being disposed in opposing relationship with each other and being resiliently urged so that their free ends are removed from each other, the tips of the free ends of the electrodes being curved toward each other.

5. The apparatus of claim 1 further comprising an additional electrode extending through said operating member and having a first end movable into and out of said opening independently out of said operating member;
    said power cable means including a wire connected to the opposite end of said additional electrode for moving said additional electrode and for supplying electric power thereto.

6. The apparatus of claim 5 wherein at least two electrodes are secured to said operating member and electrically connected in common;
    the first end of said additional electrode being positioned so that the tip thereof is positioned between the tips of the free ends of said two electrodes.

7. An electrical apparatus for treating an affected part in a coeloma comprising:
- an electrically insulating flexible tube having a distal end and a proximal end and adapted to be inserted into a coeloma, said flexible tube having an opening in its distal end;
- an electrode operating member having a first end facing said distal end of said flexible tube and a second end facing said proximal end of said flexible tube, said electrode operating member being slidably disposed within said flexible tube such that said electrode operating member can slide towards and away from said distal end of said flexible tube;
- a first and a second treating electrode, each of said treating electrodes having a free end and a base end, said base end of each of said treating electrodes being attached to said first end of said electrode operating member, said free end of each of said treating electrodes extending towards said opening in said flexible tube for movement out of or into said opening in the distal end of said flexible tube in response to movement of said electrode operating member;
- a wire assembly extending from said proximal end of said flexible tube into said flexible tube and secured to said electrode operating member for causing displacement of said electrode operating member in response to displacement of said operating wire into and out of said flexible tube, said wire assembly including a helical conductive coil having a central opening therethrough and disposed within said flexible tube and having one end coupled to said first treating electrode for supplying a high frequency current to said first treating electrode, and a conductive wire spaced from and passing into said central opening in said conductive coil and being coupled to said second treating electrode for supplying high frequency current to said second treating electrode.

8. An electrical apparatus for treating an affected part in a coeloma, comprising:
- an electrically insulating, hollow, flexible tube having a distal end and a proximal end, said tube being adapted to be inserted into a coeloma and having an opening in its distal end;
- an electrode operating member having a central passage therethrough and having a first end facing said distal end of said flexible tube and a second end facing said proximal end of said flexible tube, said electrode operating member being slidably disposed within said flexible tube, such that said electrode operating member can slide towards and away from said distal end of said flexible tube;
- a plurality of treating electrodes, each of said treating electrodes having a free end and a base end, said base end of each of said electrodes being attached to said first end of said electrode operating member, said free ends of said treating electrodes extending towards said opening in said flexible tube for movement out of or into said opening in said flexible tube in response to movement of said electrode operating member, said treating electrodes slidably engaging the periphery of said opening in said flexible tube;
- a first operating wire extending from said proximal end of said flexible tube into said flexible tube and secured to said second end of said electrode operating member for causing displacement of said electrode operating member in response to displacement of said first operating wire into and out of said flexible tube;
- a second operating wire extending from said proximal end of said flexible tube into said flexible tube and through said central passage in said electrode operating member, said second operating wire having a free end extending towards said opening in said flexible tube;
- a treating electrode in addition to said plurality of treating electrodes attached to said free end of said second operating wire for movement out of or into said opening in said distal end of said flexible tube; and
- means for supplying high frequency current to said treating electrodes.

9. An electrical apparatus according to claim 8 in which the plurality of treating electrodes are in the form of resilient rods which are formed so that their free ends are displaced from each other the tips of the free ends of the respective rods being curved toward one another.

10. An electrical apparatus according to claim 8, wherein the means for supplying current to the treating electrodes includes a power cable which is inserted into the flexible tube for supplying high frequency current to the treating electrodes.

* * * * *